US00PP36555P2

(12) United States Plant Patent
van Swieten

(10) Patent No.: US PP36,555 P2
(45) Date of Patent: Mar. 18, 2025

(54) ***PHALAENOPSIS* PLANT NAMED 'PHA484572'**

(50) Latin Name: *Phalaenopsis hybrida*
Varietal Denomination: PHA484572

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/769,820

(22) Filed: Jul. 11, 2024

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'PHA484572', characterized by its upright plant habit; moderately vigorous growth habit and moderate growth rate; strong flowering stems; strong leaves; freely flowering habit with typically three inflorescences developing per plant, each inflorescence with numerous flowers; white-colored flowers overlain with numerous dark purplish red-colored blotches and spots; and good postproduction longevity.

2 Drawing Sheets

Figure 1:
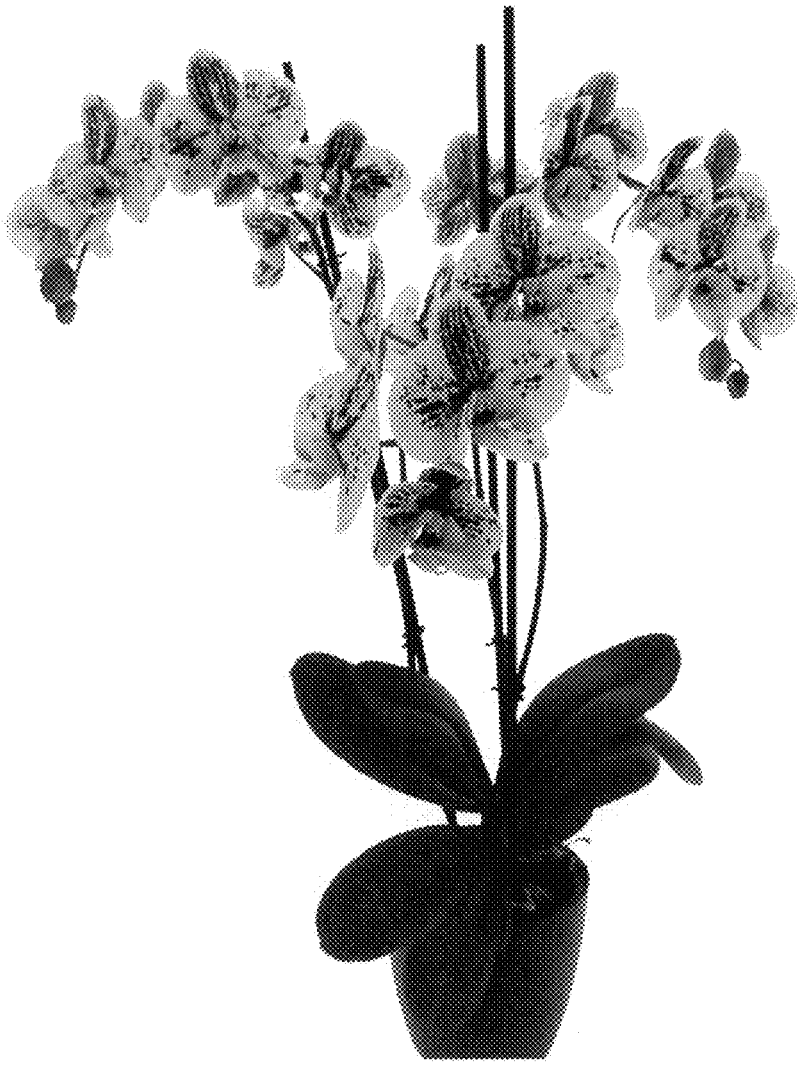

Botanical designation: *Phalaenopsis hybrida.*
Cultivar denomination: 'PHA484572'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B. V. of Bleiswijk, The Netherlands on Apr. 19, 2023, application number 2023/0887. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'PHA484572'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique and attractive patterns and coloration.

The new *Phalaenopsis* plant originated from a cross-pollination in August 2016 in Bleiswijk, The Netherlands of a proprietary selection of *Phalaenopsis hybrida* identified as code number 13-57782-02, not patented, as the female, or seed, parent with a proprietary selection of *Phalaenopsis hybrida* identified as code number 13-57782-01, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in April 2019.

Asexual reproduction of the new *Phalaenopsis* plant by in vitro meristem propagation in a controlled environment in Bleiswijk, The Netherlands since April 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA484572'. These characteristics in combination distinguish 'PHA484572' as a new and distinct *Phalaenopsis* plant:

1. Upright plant habit.
2. Moderately vigorous growth habit and moderate growth rate.
3. Strong flowering stems.
4. Strong leaves.
5. Freely flowering habit with typically three inflorescences developing per plant, each inflorescence with numerous flowers.
6. White-colored flowers overlain with numerous dark purplish red-colored blotches and spots.
7. Good postproduction longevity.

Plants of the new *Phalaenopsis* can be compared to plants of the female parent selection. Plants of the new *Phalaenopsis* differ primarily from plants of the female parent selection in flower color as flowers of plants of the new *Phalaenopsis* have smaller blotches and spots than flowers of plants of the female parent selection. In addition, petal apices of plants of the new *Phalaenopsis* are broadly obtuse whereas petal apices of plants of the female parent selection are emarginate.

Plants of the new *Phalaenopsis* can be compared to plants of the male parent selection. Plants of the new *Phalaenopsis* differ primarily from plants of the male parent selection in flower color as flowers of plants of the new *Phalaenopsis* have more blotches and spots than flowers of plants of the male parent selection. In addition, leaves of plants of the new *Phalaenopsis* are semi-erect to erect whereas leaves of plants of the male parent selection are horizontal to semi-drooping.

Plants of the new *Phalaenopsis* can be compared to plants of *Phalaenopsis hybrida* 'PHALFASXO', disclosed in U.S. Plant Pat. No. 32,322. In side-by-side comparisons, plants of the new *Phalaenopsis* differ primarily from plants of 'PHALFASXO' in the following characteristics:

1. Leaves of plants of the new *Phalaenopsis* are semi-erect to erect whereas leaves of plants of 'PHALFASXO' are semi-drooping.
2. Flowers of plants of the new *Phalaenopsis* have more blotches and spots than flowers of plants of 'PHALFASXO'.
3. Flowers of plants of the new *Phalaenopsis* have smaller blotches and spots than flowers of plants of 'PHALFASXO'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA484572' grown in a container.

Figure 2:
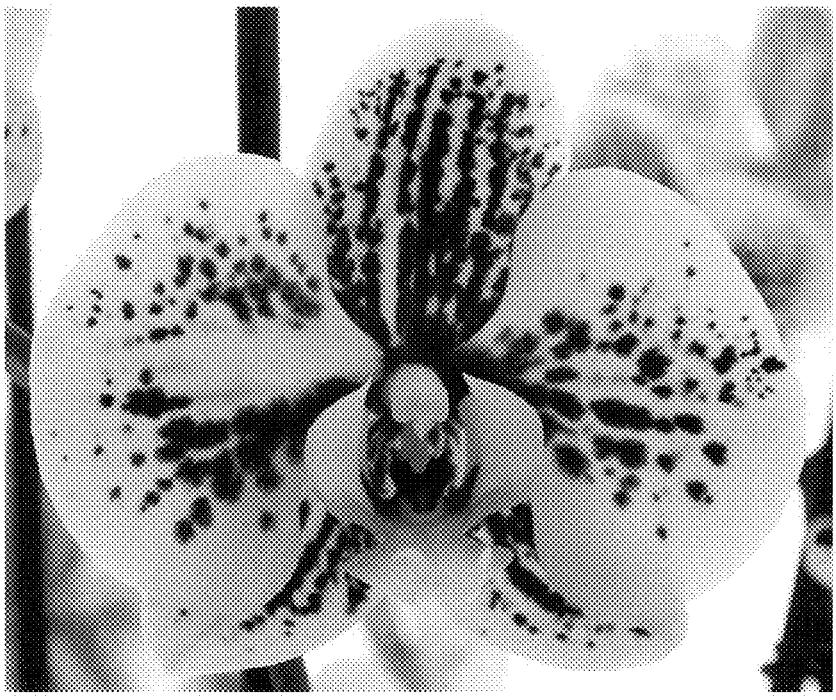

The photograph on the second sheet (FIG. 2) is a close-up view of a typical flower of 'PHA484572'.

DETAILED BOTANICAL DESCRIPTION

The aforementioned photographs and following observations and measurements describe plants grown during the autumn in 12-cm containers in a glass-covered greenhouse in Bleiswijk, The Netherlands and under cultural practices typically used in commercial *Phalaenopsis* production. Plants were 18 months old when the photographs and description were taken. During the first 14 months of production of the plants, day and night temperatures averaged 28.5° C.; and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA484572'.

Parentage:

*Female, or seed, parent*.—Proprietary selection of *Phalaenopsis hybrida* identified as code number 13-57782-02, not patented.

*Male, or pollen, parent*.—Proprietary selection of *Phalaenopsis hybrida* identified as code number 13-57782-01, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; dense.

Plant description:

*Plant form and growth habit*.—Herbaceous epiphyte; upright plant habit with typically three inflorescences developing per plant, each inflorescence with numerous flowers; monopodial; moderately vigorous growth habit and moderate growth rate.

*Plant height, substrate level to top of foliar plane*.—About 17.1 cm.

*Plant height, substrate level to top of floral plane*.—About 51.1 cm.

*Plant diameter or spread*.—About 41.3 cm.

Leaf description:

*Arrangement and quantity*.—Distichous, simple; sessile; about six fully-developed leaves per plant.

*Length*.—About 16.2 cm.

*Width*.—About 6.6 cm.

*Aspect*.—Semi-erect to erect.

*Shape*.—Obovate to elliptic-oblong; slightly carinate and slightly curled downward.

*Apex*.—Unequal obtuse.

*Base*.—Sheathing. Sheath length: About 1.6 cm. Sheath width: About 1.3 cm. Sheath color: Close to a blend of 143C and 144C.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137B with margins, close to 144B. Developing leaves, lower surface: Close to 146A and 146B with margins, close to 144B. Fully expanded leaves, upper surface: Close to a blend of 137B and 146A with margins, close to 144A and 144B; venation, close to NN137C. Fully expanded leaves, lower surface: Close to a blend of 144A and 146A with margins, close to 144A; venation, close to 143A.

Inflorescence description:

*Appearance and flowering habit*.—Showy zygomorphic flowers arranged on axillary simple or branched racemes; typically three inflorescences develop per plant; each inflorescence with about nine to ten flowers; flowers face outwardly on outwardly arching inflorescences supported by upright peduncles;

flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about ten weeks on the plant; flowers not persistent.

*Inflorescence length* (*lowermost flower to inflorescence apex*).—About 24.1 cm.

*Inflorescence width*.—About 14.5 cm.

*Flower buds*.—Height: About 1.8 cm. Diameter: About 1.4 cm by 1.7 cm. Shape: Broadly ovate. Color: Close to 145A and 145B; towards the apex, tinged with close to 197B; dots and stripes, close to N186B and N186C.

*Flower size*.—About 7.5 cm (vertical) by 8.5 cm (horizontal).

*Flower depth*.—About 3 cm.

*Petals, quantity and arrangement*.—Three, two lateral petals and one center petal transformed into a labellum.

*Lateral petals*.—Length: About 4.1 cm. Width: About 5 cm. Shape: Roughly lunate. Apex: Broadly obtuse. Margin: Entire; not undulate. Texture and luster, upper and lower surfaces: Smooth, glabrous, moderately velvety; matte. Color: When opening, upper surface: Close to NN155C; towards the margins and apex, close to 155C; randomly and heavily blotched and spotted, close to N79B and N79C; at the base, close to N79B and N79C. When opening, lower surface: Close to NN155C; towards the margins and apex, close to 155C; randomly and heavily blotched and spotted, close to N79B and N79C; at the base, close to N79B. Fully opened, upper surface: Close to NN155D; randomly and heavily blotched and spotted, close to N79B and N79C; at the base, close to N79B and N79C; color does not change with subsequent development. Fully opened, lower surface: Close to NN155D; randomly and heavily blotched and spotted, close to N79B and N79C; at the base, close to 76B; color does not change with subsequent development.

*Labella*.—Appearance: Three-parted with two lateral lobes and a central lobe. Length, lateral lobes: About 2.1 cm. Width, lateral lobes: About 1.4 cm. Length, central lobe: About 2.2 cm. Width, central lobe: About 6 mm to 19 mm. Length, cirrhose tips: About 1.7 cm. Shape, lateral lobes: Obovate. Shape, central lobe: Deltoid with a slightly elongated apex. Apex, lateral lobes: Obtuse. Apex, central lobe: Cleft with two upwardly and backwardly curled cirrhose tips and a short and broad acuminate central tip between the cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 4 mm in length, about 6 mm in width and about 6 mm in height. Color: When opening, upper surface: Lateral lobes: Close to NN155D; towards the lower margins, close to 2B; at the base, close to 59A. Central lobe: Close to 154C; towards the apex, close to 155A; at the base, close to 1D; cirrhose tips, close to 1C and 1D. Callosities: Close to a blend of N186C and 200B; at the base, close to 4C. When opening, lower surface: Lateral lobes: Close to NN155D; towards the lower margins, close to 3B; at the base, close to 182D. Central lobe: Close to 150C; towards the apex, close to 157D; at the base, close to 1D; cirrhose tips, close to 1C and 1D. Fully opened, upper surface: Lateral lobes: Close to NN155D; towards the lower margins, close to 9C; at the base, close to 59A. Central lobe: Close to 2B; towards the apex, close to NN155D; towards the base, close to a blend of N186C and 200B and at the base, close to NN155D; cirrhose tips, close to 8B. Callosities: Close to a blend of N186C and 200B; at the base, close to 8A and 8B. Fully opened, lower surface: Lateral lobes: Close to NN155D; towards the lower margins, close to 6C; at the base, close to N75B to N75D. Central lobe: Close to 151D; towards the apex, close to NN155D; at the base, close to 155D; margins, close to 152D; cirrhose tips, close to 8B.

*Sepals*.—Quantity and arrangement: Three, one upper dorsal sepal and two lower lateral sepals. Length, dorsal sepal: About 4.3 cm. Width, dorsal sepal: About 3.1 cm. Length, lateral sepals: About 4.5 cm. Width, lateral sepals: About 2.7 cm. Shape, dorsal sepal: Oblong to broadly elliptic. Shape, lateral sepals: Ovate. Apex, dorsal sepal: Retuse. Apex, lateral sepals: Bluntly acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to NN155C; towards the margins and apex, close to 155C; heavily blotched and spotted with close to N79B and N79C; at the base, close to N79B. When opening, lower surface: Close to 145C; towards the margins and apex, close to 157B; heavily blotched and spotted with close to N77A to N77C; at the base, close to N77A. Fully opened, upper surface: Close to NN155D; heavily blotched and spotted with close to N79B and N79C; at the base, close to N79B and N79C. Fully opened, lower surface: Close to 76B; towards the margins and apex, close to N155D; heavily blotched and spotted with close to N77A to N77B; at the base, close to N77A and N77B. Color, lateral sepals: When opening, upper surface: Close to 157A; towards the upper margin, close to 157B; heavily blotched and spotted with close to N79B and N79C; at the base, close to N79B. When opening, lower surface: Close to a blend of 152D and 195B; heavily blotched and spotted with close to N77A to N77C; at the base, close to N77A. Fully opened, upper surface: Close to NN155D; heavily blotched and spotted with close to N79B and N79C; at the base, close to N79B and N79C. Fully opened, lower surface: Close to N155B; towards the base, close to a blend of 76D and NN155B; heavily blotched and spotted with close to N77A to N77B; at the base, close to N77A and N77B; main vein tinged proximally with close to 70B.

*Peduncles*.—Length: About 54.5 cm. Diameter: About 5 mm. Strength: Strong. Aspect: Upright to outwardly arching. Texture and luster: Smooth, glabrous; matte. Color: Close to 143A; heavily dotted with fine dots, close to 147A.

*Pedicels*.—Length: About 3.6 cm. Diameter: About 3 mm. Strength: Moderately strong. Aspect: About 60° from peduncle axis. Texture and luster: Smooth, glabrous; matte. Color: Close to 146D; proximally, close to N186C and distally, close to 182D.

*Reproductive organs*.—Androecium: Column length: About 9 mm. Column width: About 6 mm. Column color: Close to NN155D; at the base, close to N78A and N78B. Pollinia quantity: Two. Pollinia diameter (per two pollinia): About 2.5 mm. Pollinia color: Close to 23A. Gynoecium: Stigma length: About 3 mm. Stigma width: About 4.5 mm. Stigma shape: Reniform. Stigma color: Close to N155A. Ovary length: About 6 mm. Ovary diameter: About 1 mm. Ovary color: Close to 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA484572' as herein illustrated and described.

* * * * *